United States Patent [19]

Bader et al.

[11] 4,452,246

[45] Jun. 5, 1984

[54] SURGICAL INSTRUMENT

[76] Inventors: Robert F. Bader, 8 Elfin, Iloine, Calif. 92714; Dennis P. Kerkoff, 12752 Melody Dr., Garden Grove, Calif. 92641

[21] Appl. No.: 304,210

[22] Filed: Sep. 21, 1981

[51] Int. Cl.$^3$ .............................................. A61B 17/06
[52] U.S. Cl. ..................................... 128/340; 128/318; 128/321; 7/135; 30/254; 30/131
[58] Field of Search ............... 128/318, 321, 322, 346, 128/325, 340; 30/131, 254, 230, 256, 122; 7/131, 135; 81/318, 324, 321

[56] References Cited

U.S. PATENT DOCUMENTS

| | | | |
|---|---|---|---|
| 2,315,326 | 3/1943 | Gmeiner | 128/340 |
| 2,853,074 | 9/1958 | Olson | 128/322 |
| 3,175,556 | 3/1965 | Wood et al. | 128/346 X |
| 3,443,313 | 5/1969 | Profy | 128/321 X |
| 4,271,838 | 6/1981 | Lasner et al. | 128/318 |

FOREIGN PATENT DOCUMENTS 1299412  6/1962  France ................... 81/321

Primary Examiner—Michael H. Thaler
Attorney, Agent, or Firm—Leo R. Carroll

[57] ABSTRACT

A surgical instrument is provided which has independent capabilities of operating as a surgical needleholder for suturing operations, and as a surgical cutting device for severing the suture thread. The instrument of the invention may be operated as a conventional needleholder and, to that end, it has a pair of jaws in which a suture needle may be securely held for the suturing operation, and it also has a usual clasp mechanism for locking the jaws in their closed position. However, in accordance with the concepts of the invention, one of the arms of the instrument is split into two co-extensive elongated sections, both being pivoted at the pivot point of the instrument. The distal end of the first section is formed into one of the jaws of the instrument, and that arm functions with the other arm of the instrument to perform the conventional needle holding function. The second section of the split arm has a scissor blade formed integral with its distal end, and that scissor blade cooperates with a blade formed on the adjacent jaw to perform the cutting function. The first section is coupled to the other arm of the instrument by the aforesaid clasp mechanism, so that the suture needle may be clamped in the jaws of the instrument while the scissor blades are being independently operated to cut the suture thread.

2 Claims, 6 Drawing Figures

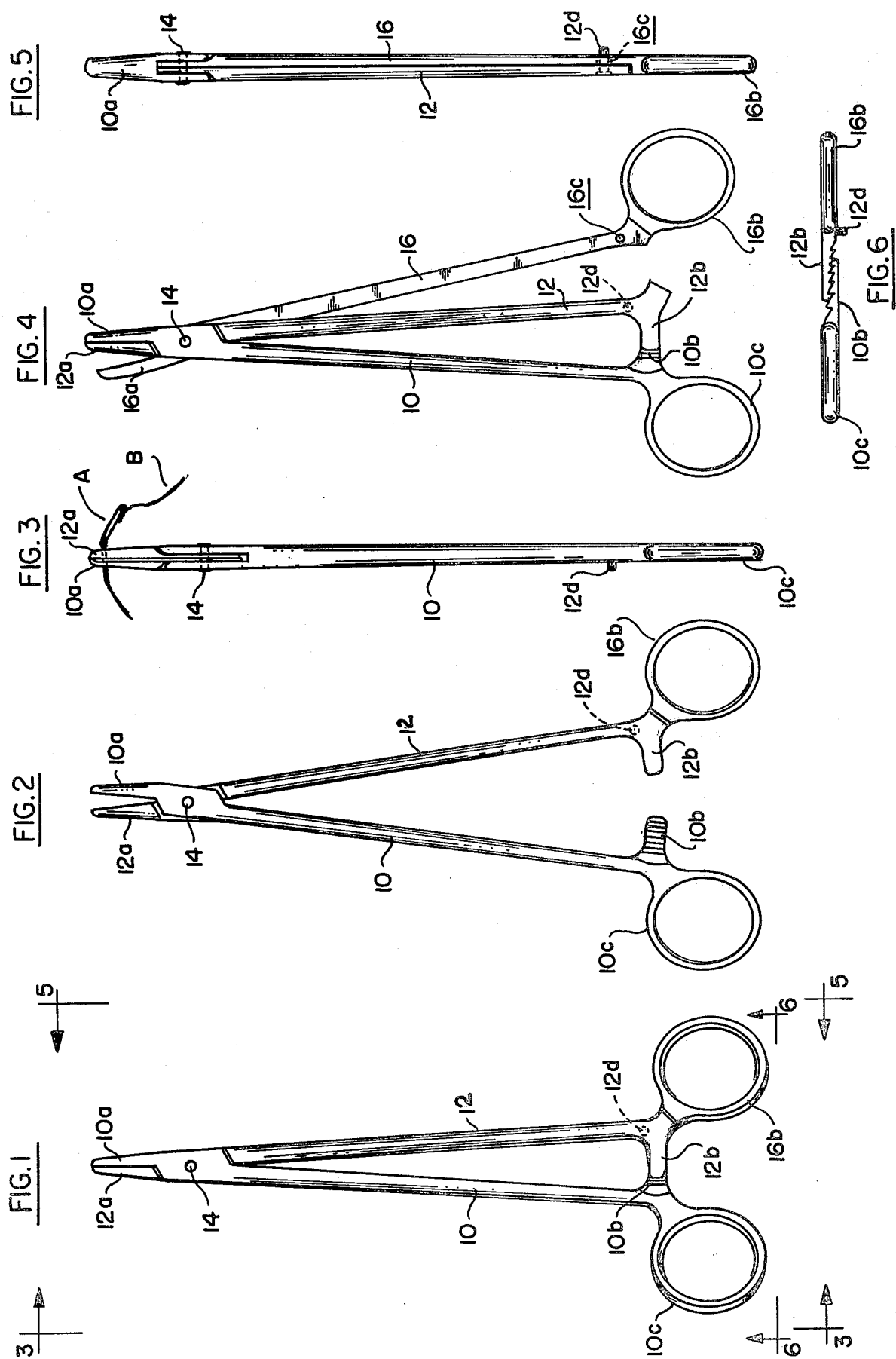

SURGICAL INSTRUMENT

BACKGROUND OF THE INVENTION

The surgical needleholder is a well known instrument by which a surgeon, or other medical operator, manipulates a surgical suture needle through either the skin or underlying tissue of a laceration being sutured, accurately to draw the edges of the laceration together with surgical suture thread. Surgical needleholders are disclosed, for example, in U.S. Pat. No. 2,863,459; No. Re 22,857 and No. 1,579,379. As described in those patents, the conventional surgical needleholder is composed of stainless steel and is essentially in the form of a specialized pair of pliers. By the use of the instrument, the surgeon may secure the suturing needle in the jaws of the instrument, and the instrument serves to guide the suturing needle to cause the needle to pierce the skin edges adjacent to the laceration, so that the edges may be drawn and held together by the suturing thread which is bonded to the needle. In this manner, the suture thread serves to close the laceration, with the apposition of the skin on either side of the laceration being achieved by the ligation of several knots.

Surgical suture material is usually packaged as a sterile length of thread, approximately 18 inches in length, which has been previously bonded to a usually curved, sharp surgical needle. After each stitch has been completed during a suturing operation, it becomes necessary to cut the unused length of the suture thread, so that the unused thread may be utilized for subsequent stitches, and so that the stitches may each be physically separate from one another.

It is the present prior art practice to cut the suture thread during the suturing operation with a separate pair of stainless steel surgical scissors. However, this entails a cumbersome sequence of manual operations for the surgeon. For example, for a right-handed person, the needleholder which has been operated by the right hand during the suturing operation, must now be transferred to the left hand, the left hand having previously been used to hold a pair of surgical forceps so as to draw the skin edges together into the proper position to enable the suturing operation to be performed. Accordingly, in following the prior art practice, at the commencement of the cutting operation, the surgeon holds two instruments in his non-working left hand, and he must now pick up the scissors with his right hand in order to cut the thread.

The operation in picking up the scissors can become troublesome in that they may be located on a remote surgical tray, and they may be hidden under other instruments, so as not to be readily available. This, at the very least, creates a measure of distraction for the surgeon from the performance of the surgical process itself.

When the scissors have been located, in accordance with the prior art practice, they are held in the working right hand of the surgeon, and are used to sever the suture thread at a visually determined length from the knots, for example, from ⅛"-½". When the thread has been cut, the scissors must be returned to the surgical tray, or other location. In either event, there is a likelihood that the scissors may accidentally fall to the floor, or to another non-sterile surface, thereby necessitating the production of a new pair of scissors.

When the scissors have been returned to the surgical tray, or other location, the needleholder must now be returned to the right working hand, in carrying out the prior art practice, so that the next stitch may be commenced. The above described sequence of hand transfers of the instruments becomes even more troublesome when many stitches are to be inserted in the patient. For instance, in a long plastic surgical procedure requiring, for example, 40 stitches, forty sequences of instrument transfers must be performed.

In an attempt to avoid the sequences of instrument transfers described in the preceding paragraphs, combined needleholder/scissor instruments have been devised in the prior art. One such instrument is disclosed, for example, in U.S. Pat. No. 2,315,326. There are actually two popular types of combined needleholder/scissor instruments in the prior art.

In a first type of prior art instrument, a pair of opposing flat jaw surfaces are provided at the distal end of the instrument, while the working surfaces nearer the pivot pin are shaped as a pair of blades which operate as scissors.

However, the type of prior art instrument described above has inherent drawbacks. Specifically, the needle holding and thread cutting functions of the instrument are not independent of one another; so that when the cutting blades are being used, there is no needle holding capability, and the needle must therefore be held between the fingers of the operator. Moreover, as the blades of the instrument are being closed to cut the thread, the operator must be careful not to accidentally compress and destroy living tissue by the jaws of the instrument. Also, this particular type of prior art instrument does not possess a clasp mechanism to secure the needle while the suturing operation is being carried out, and the operator must always apply a closing force with his fingers, in order that the needle may be firmly held in the jaws of the instrument.

In a second type of prior art instrument which combines the needle holding and scissor functions, a cutting notch is provided on the outer side of the needle holding jaw. This latter type of instrument is provided with a clasp mechanism in order that the needle may be securely held in the jaws of the instrument when the jaws are closed. To cut the thread, the instrument is positioned so that the notch receives the thread at the point to be severed, and the instrument is squeezed so that the clasp moves to a tighter locked position, and when that occurs a blade moves across the notch to sever the thread.

When the latter prior art combination instrument is used, the cutting process does not possess the fine feel of a pair of scissors. In addition, the cutting operation is complicated by the fact that a substantial portion of the distal end of the instrument must be inserted into the wound in order to position the cutting notch properly to receive the thread, and this has dangerous implications.

The combined needleholder/cutter of the present invention is advantageous in that it obviates the need for two separate instruments in order to perform the needle holding and thread cutting functions. Also, the instrument of the present invention, as will become more apparent as the present description proceeds, has certain advantages over the prior art combination instruments in that the cutting function may be carried out independently of the needle holding function, and without any of the drawbacks of either of the prior art combination instruments.

Accordingly, a principal objective of the present invention is to combine the various instruments usually employed during suturing operations into a single instrument, so as to enable such operations to be performed with increased convenience and in less time. A feature of the instrument of the invention is that it is practically identical in configuration with needleholders presently being used so that a doctor accustomed to using the prior art instrument will have little trouble in adapting himself to the use of the combination instrument of the invention.

BRIEF DESCRIPTION OF THE DRAWINGS

FIG. 1 is a top plan view of the surgical instrument of the present invention, in one of its embodiments, and shown with its jaws in a closed and latched position;

FIG. 2 is a view, like FIG. 1, but with the jaws in their open position;

FIG. 3 is a side view of the instrument of FIG. 1, taken essentially along the line 3—3 of FIG. 1;

FIG. 4 is a top plan view of the instrument of FIG. 1, but with the cutting arm released, so that a suture cutting operation may be performed independently of the needle holding function, and while the instrument is still holding the needle;

FIG. 5 is a side view of the instrument of FIG. 1, taken essentially along the line 5—5 of FIG. 1; and FIG. 6 is an end view of the instrument, taken along the line 6—6 of FIG. 1.

DETAILED DESCRIPTION OF THE ILLUSTRATED EMBODIMENT

The surgical instrument shown in the drawing includes a pair of crossed arms 10 and 12 which are pivoted by a rivet or screw 14 at a pivot point. The arms 10 and 12 form respective jaws 10a and 12a at one end of the instrument for holding a needle A (FIG. 3) to which a suture thread B is bonded, when the jaws are in the closed position of FIG. 1.

The jaws are held in their closed position by a first clasp mechanism which is well known to the art, and which includes serrated projections 10b on arm 10 that engage serrated projections 12b on arm 12 (FIG. 6). As the jaws of the instrument are closed, as shown in FIGS. 1 and 6, the serrations on the two projections engage one another in a latching relationship, and hold the instrument in its closed condition until the two arms are physically moved in opposite directions to one another perpendicular to the plane of the paper in FIG. 1, to release the projections.

In accordance with the present invention, a third arm 16 (FIGS. 4 and 5) is pivotally coupled to arms 10 and 12 at the pivot point by the screw or rivet 14. Arm 16 has a scissors blade 16a formed at its end adjacent to the jaw end of the instrument, and jaw 12a has a further scissors blade (not shown) formed to cooperate with blade 16a in a scissors action when arm 16 is pivotally moved about the pivot point.

Arm 10 has a looped handle 10c formed at its end opposite to jaw 10a, and arm 16 has a looped handle 16b formed in its opposite end from blade 16a.

The arm 16 is held in co-extensive relationship with arm 12 by a latching means which comprises, for example, a stud 12 (FIGS 3, 5 and 6) on arm 12 which is received in a hole 16c in arm 16 when the two arms in the position shown in FIGS. 1, 2 and 5, with arm 16 extending under arm 12.

When arms 12 and 16 are latched together by the latching means 12d, 16c the instrument may be operated in a manner identical to the prior art needleholders, by which, when the handles 10c and 16b are moved from the position shown in FIG. 1 to the position shown in FIG. 2, the jaws 12a and 10a may be opened to receive the needle A (FIG. 3). Then, the handles 16b and 10c may be moved back together to the position shown in FIG. 1, at which position they are latched by the latching means 10b, 12b to grasp needle A.

After the appropriate knots have been tied, arm 16 may be released from arm 12 by moving the arm 16 downwardly with respect to arm 12 to release the latching means 12d, 16c, so that, while the jaws 10a and 12a are still closed and grasping the needle A, arm 16a may be independently moved to the position shown in FIG. 4, and then moved back to cause blade 16a to cut the suture thread. Arm 16 may again be latched with arm 12, and the needle holding operation may be continued without any need to release the needle, or to lay down the suturing instrument in order to cut the thread.

It will be appreciated that the instrument of the invention has the external form of a conventional prior art surgical needleholder. However, on closer inspection, and as described above, several unique features are present in the instrument of the invention. Firstly, the upper of the two operating arms is split into two co-extensive sections, both of the sections being pivoted by the central pivot pin of the instrument. The two sections are normally held together by the pin/hole combination described above, or by an equivalent releasable latching mechanism. As each arm of the instrument of the invention extends past the pivot point, other features become apparent. Specifically, the distal end of one of the two sections of the split arm becomes one of the jaws of the instrument and faces the second jaw formed at the end of the undivided arm. The distal end of the second section of the split arm becomes a scissor blade which cooperates with a second scissor blade formed integral with the adjacent jaw.

The instrument of the invention, when operating as a needleholder is usually operated by the user's thumb and fourth finger. When the needle holding function is to be carried out, the fourth finger and thumb are used to open and close the jaws of the instrument in exactly the same way as a conventional prior art needleholder. When the cutting function is to be performed, the clasp mechanism is locked, and the pin/hold combination is disengaged so that the two sections of the split arm may be moved independently to open and close the cutting blades while the needle holding jaws are locked in a closed position. When the suture thread is cut, the pin/hold combination is again engaged so that the needle holding function may be resumed.

The invention provides, therefore, a simple and inexpensive surgical instrument which combines a surgical scissors with a surgical needleholder, in which both functions may be carried out independently of one another, and which may be operated easily and conveniently, as described above.

It will be appreciated that while a particular embodiment of the invention has been shown and described, modifications may be made, and it is intended in the following claims to cover all modifications which come within the spirit and scope of the invention.

What is claimed is:

1. A surgical instrument including a pair of crossed arms pivotally coupled to one another at a pivot point, said arms forming jaws at one end of the instrument for holding a needle, first means coupled to the arms for releasably latching the jaws to cause the jaws to grip the needle, a third arm pivotally coupled to the crossed arms and having a cutting blade at said one end of said instrument, second means coupled to said third arm and to one of said crossed arms for releasably latching said third arm in a co-extensive position adjacent to one of said crossed arms, said one of said crossed arms having a cutting blade formed opposite said jaw at said one end of said one crossed arm to engage the cutting blade of said third arm in a scissors action when said third arm is operated for cutting suture thread independently of said crossed arms when said jaws are latched by said first means.

2. The instrument defined in claim 1, in which said third arm has a first looped handle formed at one end thereof, and the other of said crossed arms has a second looped handle formed at one end thereof.

* * * * *